United States Patent [19]

Rogers

[11] 4,125,442

[45] Nov. 14, 1978

[54] ARTIFICIAL TEETH CONSTRUCTION

[76] Inventor: Olbert W. Rogers, 70 Gymea Bay Rd., Gymea, New South Wales 2227, Australia

[21] Appl. No.: 722,291

[22] Filed: Sep. 10, 1976

[51] Int. Cl.$^2$ .......................... A61C 5/08; C25D 5/34
[52] U.S. Cl. ...................................... 204/38 C; 32/12;
204/32 R; 427/330; 427/376 C; 427/405; 427/406
[58] Field of Search ..................... 204/38 C, 32 R, 34;
32/12; 427/330, 376 C, 405, 406; 29/195; 75/165

[56] References Cited

U.S. PATENT DOCUMENTS

| | | | |
|---|---|---|---|
| 1,782,552 | 11/1930 | Supplee | 32/12 |
| 2,569,453 | 10/1951 | Chester et al. | 148/6.17 |
| 2,819,207 | 1/1958 | Shepard | 204/38 |
| 2,980,998 | 4/1961 | Coleman et al. | 32/12 |
| 3,585,064 | 6/1971 | Prosen | 117/70 C |

OTHER PUBLICATIONS

Modern Electroplating; Frederick A. Lowenheim, editor; John Wiley & Sons, Inc; New York, 1963, p. 434.

*Primary Examiner*—John H. Mack
*Assistant Examiner*—William Leader
*Attorney, Agent, or Firm*—Hill, Gross, Simpson, Van Santen, Steadman, Chiara & Simpson

[57] ABSTRACT

Composite metal/porcelain tooth reconstructions are manufactured by bonding porcelain to a basis metal which is pretreated by electrolytically depositing thereon a thin layer of a different metal. The pretreatment has the effect of increasing the bond strength between the metal and the porcelain.

If the basis metal is a noble metal, the different metal may be deposited directly, and the porcelain then bonded on. If the basis metal is a base metal the pretreatment preferably includes an etching step, deposition of a preliminary metal layer on the etched surface, followed by deposition of the main metal layer, followed by a final deposition of metal prior to bonding to the porcelain.

7 Claims, 8 Drawing Figures

ARTIFICIAL TEETH CONSTRUCTION

This invention relates to the manufacture of artificial tooth reconstructions of porcelain and metal composites.

In my earlier U.S. patent application Ser. No. 570,740, filed on Apr. 23, 1975, I described a method of making a porcelain tooth reconstruction involving the prior manufacture of a thin metal model into which porcelain is fused layer by layer to produce a procelain insert corresponding accurately to a tooth cavity into which it may subsequently be secured adhesively by means of a conventional dental cement.

It is an object of the present invention to produce composite metal and porcelain tooth reconstruction suitable either for endosseous implantation in bone tissue or for capping an existing tooth stump.

Composite metal/porcelain reconstructions in themselves are not new; however, a serious problem exists in that current techniques for bonding porcelain to metal are generally unreliable and the effectiveness of such bonds is a matter of dispute and concern and is discussed for example by Fraunhofer, *Scientific Aspects of Dental Materials*, Butterworths 1975, at page 316.

Metals used in the production of metal/porcelain reconstructions include gold, platinum, gold alloys and base metals, usually chromium alloys such as nichrome. Gold suffers the obvious disadvantage that is expensive as also are gold alloys and platinum. Chromium alloys have better physical properties than gold, particularly in terms of specific gravity, and are less expensive; however, the bond between them and porcelain formed by current techniques is even less satisfactory than between gold and porcelain.

Examples of such bonds are shown in the accompanying FIGS. 1 to 4 in which.

Figure 1:
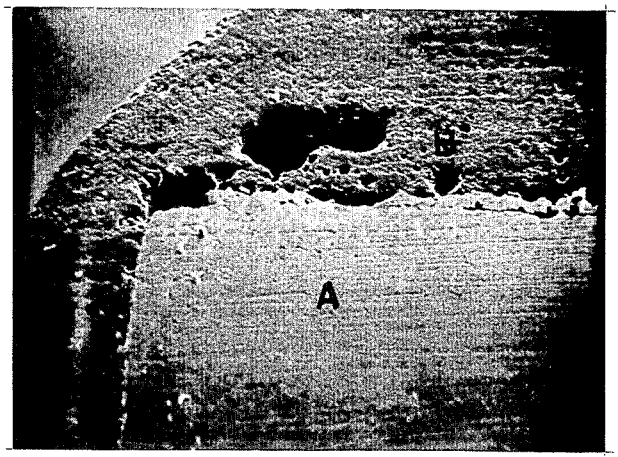
FIG. 1 illustrates a bond between "Victory" (Trademark) metal and porcelain at a magnification of 150.
Figure 2:
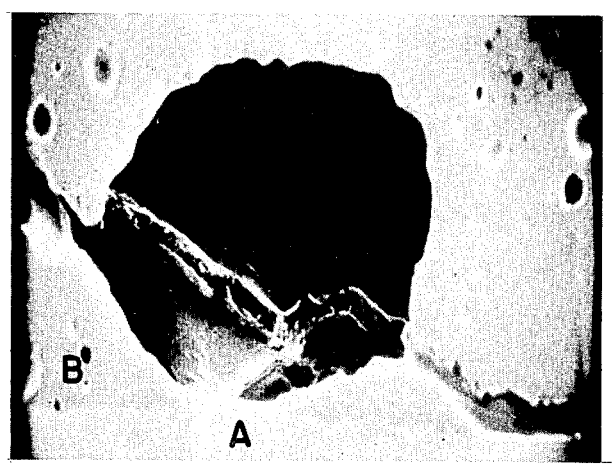
FIGS. 2 and 3 illustrate bonds between "Ultratek" (Trademark) metal and porcelain also at a magnification of 150.
Figure 3:
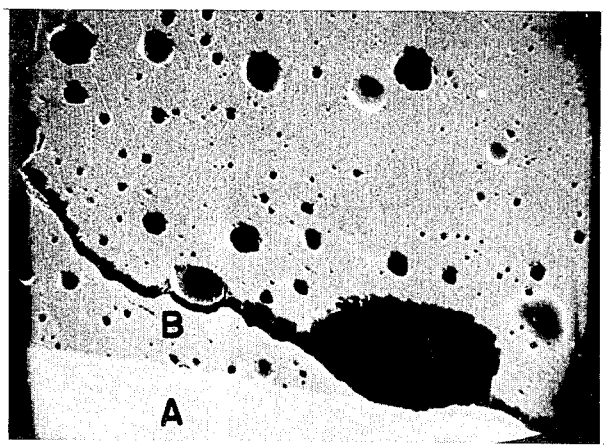
Figure 4:
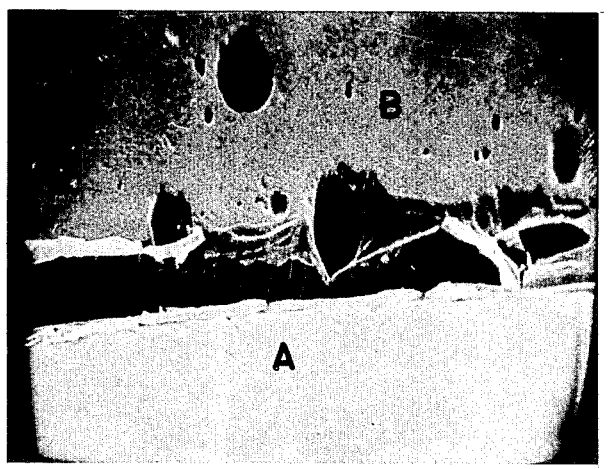
FIG. 4 illustrates a bond between "Ultratek" and porcelain at a magnification of 200.

In these illustrations the unsatisfactory bond between the metal A and porcelain B can be seen; note in particular the stress concentration fracture lines in FIGS. 2, 3 and 4.

According to the present invention strong and reliable bonding can be obtained between metal and porcelain to permit the manufacture of tooth reconstructions as aforesaid, using either noble or base metals to support the porcelain.

The invention also permits the production of tooth reconstructions either (a) by building up layers of porcelain on the basis metal, or (b) by bonding a preformed porcelain facing to the basis metal.

Technique (a) is suitable for producing endosseous implants, and also as is technique (b), suitable for producing tooth crowns.

According to the invention therefore, in the manufacture of metal/porcelain tooth reconstructions, the basis metal is pretreated before being bonded to the porcelain by depositing thereon a thin coating of a different metal.

The precise form of pretreatment will depend upon the nature of the basis metal, and in particular noble and base metal require different handling.

In the case of noble metals, that is gold alloys and platinum, (pure gold being only infrequently employed because of its softness), a thin coating of pure gold, platinum, palladium, iron, tin, zinc, copper, nickel, chromium, cobalt, or indium is applied to the basis metal, preferably electrolytically and preferably in a thickness between 10 and 30 microns. Thereafter the porcelain may be bonded thereto by the procedure described in greater detail hereinafter.

In the case of base metals however, such as the conventionally used chronium alloys, the deposition of the different metal coating must be conducted in conjunction with additional surface treatments in order to secure a satisfactory bond with the porcelain later.

A number of alternative pretreatments may be applied to the base metal prior to the deposition of the metal coating including, for example:

(i) etching with acid, such as 5–50% sulphuric acid at 5 amps/sq.ft. for 1 to 5 minutes;

(ii) anodic etching for about 3 minutes followed by cathodic activation for about 60 minutes using Wood's nickel electrolyte at 30 amps/sq.ft.; or (iii) anodic etching for about 2 minutes followed by cathodic activation for about 2 to 10 seconds using 10–50% sulphuric acid at 10–200 amps/sq.ft.

The current density and concentration of electrolyte may be varied having regard to the resistance to passivation of the metal alloy employed.

In addition to the improved bonding achieved by the metal deposit, in the case of base metals such deposit forms a barrier to the formation of undesirable oxides such as chromium and nickel oxides which can reduce the thermal coefficient of expansion of the ceramic by as much as 50%, as well as causing unsightly discoloration.

If the anodic pretreatment method is employed, in order to improve the bonding of the main metal layer, it is desirable to apply a thin coating, preferably electrolytically, of a still different metal before depositing the main layer. Gold or platinum is preferred as the main layer, while for the prior additional layer, tin, silver, iron, zinc, copper, or indium may be used.

Following the deposition of the gold or platinum, in order to improve the bond with the porcelain, yet a further thin layer of a different metal is applied, preferably electrolytically, for example of iron, tin, zinc, copper, cobalt, platinum or palladium.

To the basis metal thus treated, i.e. by simple deposition in the case of noble metals, or the more complex pretreatment and deposition procedure described in the case of base metals, porcelain may now be bonded. The method of bonding porcelain will depend upon the reconstruction required and whether a preformed porcelain facing is to be employed or whether the complete porcelain facing is to build up in layers on the basis metal structure.

The use of preformed porcelain facings would of course have obvious economic advantages since a wide range of such facings of various shapes and sizes could be mass-produced very cheaply; however, a problem arises in adapting mass-produced porcelain pieces to the infinite variety of contours and colours encountered when treating the teeth of different patients.

The present invention overcomes this difficulty and permits accurate reconstructions using preformed porcelain pieces to be produced corresponding with precision to a tooth to be treated.

This aspect of the present invention is particularly adapted to the manufacture of reconstructions in the form of crowns or caps comprising a metal "thimble" adapted to fit over a tooth stump, to the front of which "thimble" a porcelain facing is attached so that when fixed in the patient's mouth only the porcelain facing is visible.

Thus a model of a tooth stump to be treated is prepared in conventional manner, for example from a plaster material commonly referred to as "artificial stone".

A porcelain facing of the desired colour shade and approximating to the frontal contours of the tooth stump model is then selected, and the rear of such facing is ground to conform reasonably closely to the front surface of the model. It will be appreciated that although by grinding the facing in this way a good approximation to the frontal contours of the model can be achieved, it is virtually impossible to produce a contour sufficiently accurate to permit such facing to be affixed satisfactorily to the model, and certainly it is impossible to do so economically.

The model is then waxed and the porcelain facing is stuck onto the front of the model and is retained in position by means of the wax. In a preferred embodiment a thin metal or other "spacer" is located to provide space for a coating of porcelain material to be applied subsequently as hereinafter described.

By means of the "lost wax" principle, a metal "thimble" is then cast. The thimble so produced will accurately fit over the tooth stump in the patient's mouth and can therefore ultimately be cemented over such stump in the usual way.

The porcelain facing is now bonded to the metal thimble as hereinafter described; it will be appreciated that the facing cannot be merely cemented to the thimble as a quite inadequate bond is thereby achieved.

Thus the thimble is pretreated by the methods described hereinbefore according to whether the thimble is made from noble or base metal.

To the front of the thimble thus treated, a layer of porcelain paste is applied to which the porcelain facing is applied. The assembly is then fired to bond the facing and the thimble firmly together.

The technique described permits the formation of a high quality bond between the thimble and the porcelain facing not hitherto possible, as well as permitting the use of mass-produced porcelain facings, either glazed or unglazed, the bond achieved with the latter being even better. The use of a platinum deposit rather than a gold deposit also permits the use of the harder high-fusion porcelain.

The deposited layer of metal or metals on the basis metal appears to act as a "buffer" zone between the basis metal and the porcelain, which zone absorbs the stresses caused by differences in the coefficients of thermal expansion between the basis metal and the porcelain as it cools from the firing temperature to ambient temperature.

Figure 5:
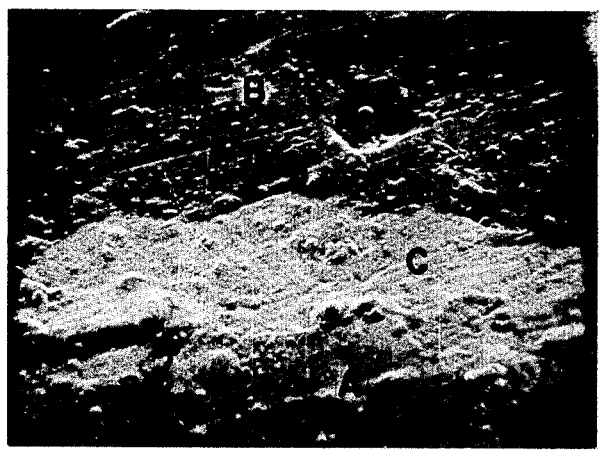
Figure 6:
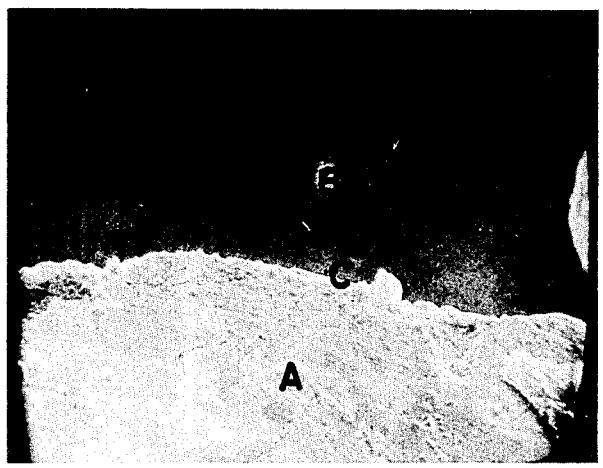

The improved bonding obtained by the method of the invention is illustrated in the accompanying FIGS. 5 and 6 in which:

FIG. 5 illustrates a bond between "Victory" metal A and porcelain B with the interposition of electrolytically deposited layer of gold C, at a magnification of 3000. In the example illustrated here the "Victory" metal surface was initially treated by anodic etching in Wood's electrolyte as hereinbefore described and thereafter gold was electrolytically deposited thereon. A further layer of tin was electrolytically deposited on the gold prior to the bonding with the porcelain.

FIG. 6 illustrates a bond between "Ultratek" metal A and porcelain B with the interposition of electrolytically deposited layer of gold C at a magnification of 3000. In this example the "Ultratek" metal was pretreated in the same manner as the metal in FIG. 5.

Figure 7:
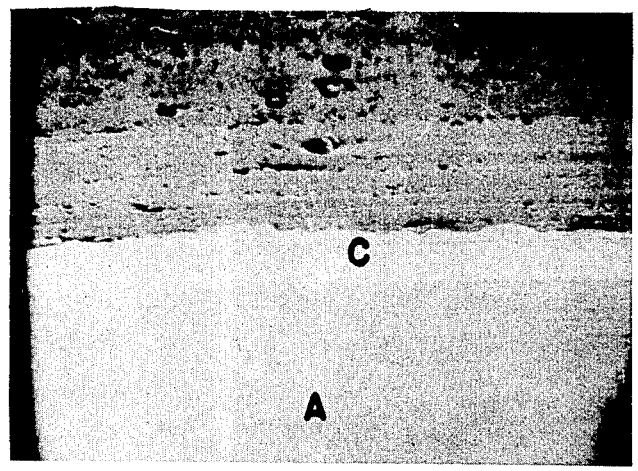
Figure 8:
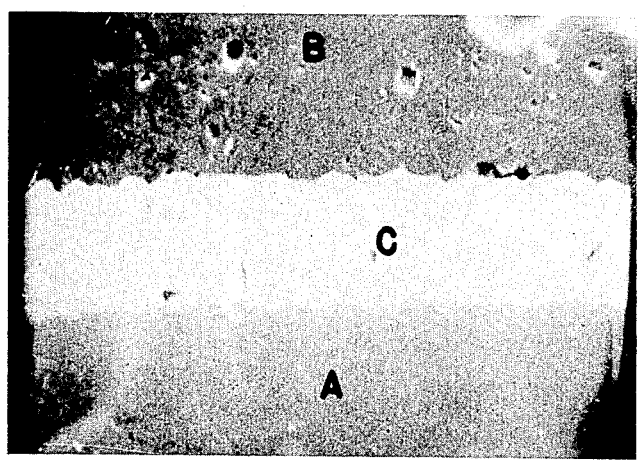

The manner in which the mis-matchings of thermal coefficients of expansion are absorbed by the deposited metal layer are illustrated in FIGS. 7 and 8 in which porcelain is bonded to an 18/8 stainless steel according to the methods previously described. The coefficient of expansion of the steel is $17.0 \times 10^{-6}$ while that of the porcelain is $10.0 \times 10^{-6}$.

The invention is further illustrated by reference to the following specific examples.

EXAMPLE 1

A nichrome thimble was cast around a tooth stump model and then activated by placing in 15% sulphuric acid, anodically treating at 200 amps/sq.ft. for 2 minutes and then cathodically treating for 3 seconds. The thimble was then rinsed in water and placed in a gold cyanide electrolyte solution for 15 minutes at a current density of 30 amps/sq.ft. at 60° C. to deposit a layer of gold. The composition of the electrolyte was as follows:

Potassium gold cyanide 14.1 g
Potassium cyanide 18.3 g
Potassium carbonate 14.1 g
Boric acid 11.4 g
Distilled water to 1 liter The treatment resulted in deposition of a gold layer approximately 0.001 inch thick.

After further rinsing with water the thimble was placed in electrolyte having the following composition:

Sodium stannate 15 g
Sodium hydroxide 135 g
Distilled water 1 liter

The temperature was maintained at 60° C. and tin was deposited at a current density of 15 amps/sq.ft. for 1 minute.

The porcelain material was then built up on the thus treated metal surface in a vacuum furnace using two opaque firings at 905° C., two firings at 845° C. and using V.M.K. 68 porcelain, with final vitrification at 875° C. not under vacuum.

EXAMPLE 2

In this example a preformed porcelain facing ws empolyed using a metal thimble pretreated as described in Example 1. However, instead of building up porcelain layer by layer as described in Example 1, a pretreated porcelain facing was luted to the treated metal surface with opaque porcelain and then fired at 875° C. for 10 minutes.

The method described according to the present invention is ideally suited to the production of aesthetic tooth reconstruction of various types providing ideal biocompatibility and high strength.

I claim:

1. A method for use in constructing composite metal-porcelain tooth and/or bone reconstructions, the basis metal being a chromium alloy comprising the steps of pretreating the basis metal by etching, the etching being conducted anodically, followed by cathodic activation depositing a first layer of metal on said basis metal, said first layer of metal being selected from the group consisting of tin, silver, iron, zinc, copper and indium; further depositing on said first metal layer a second metal layer, said second layer of metal being selected from the group consisting of gold alloys and platinum; and bonding porcelain thereto.

2. A method according to claim 1 wherein prior to the bonding of the porcelain a third layer of metal is deposited on said second layer, said third layer being selected from iron, tin, zinc, copper, cobalt, platinum or palladium.

3. A method according to claim 1 wherein said porcelain bonded to the pretreated basis metal is a preformed porcelain facing.

4. A method according to claim 1 wherein said porcelain bonded to the pretreated basis metal is built up layer by layer.

5. A method according to claim 1 wherein said step of depositing a first layer of metal and said step of depositing a second layer of metal are both conducted electrolytically.

6. A method according to claim 1 wherein said steps of anodic etching and cathodic activation are performed in an electrolyte comprising 10%–50% sulfuric acid.

7. A method according to claim 6 wherein said step of cathodic activation is performed for 2–10 seconds at a current density of 10–200 amps per square foot.

* * * * *